United States Patent [19]

Gómez-Pamo et al.

[11] Patent Number: 5,324,652

[45] Date of Patent: Jun. 28, 1994

[54] PREPARATION OF PEPSIN SUBSTANTIALLY DEVOID OF PROTEOLYTIC ACTIVITY USING DIALYSIS

[75] Inventors: Antonio G. Gómez-Pamo; Aurora Brieva Delgado; Juan P. Pivel Ranieri, all of Madrid, Spain

[73] Assignee: Laboratorios Andromaco SA, Madrid, Spain

[21] Appl. No.: 973,158

[22] Filed: Nov. 6, 1992

[30] Foreign Application Priority Data

Nov. 8, 1991 [ES] Spain .................... P9102474

[51] Int. Cl.⁵ .................... C12N 9/50; C12N 9/64; C12N 9/48; A61K 37/54

[52] U.S. Cl. .................... 435/219; 424/94.66; 435/212; 435/226

[58] Field of Search .................... 424/94.66; 435/219, 435/226, 212

[56] References Cited

U.S. PATENT DOCUMENTS

| | | | |
|---|---|---|---|
| 414,591 | 11/1889 | Russell | 435/226 |
| 424,357 | 3/1890 | Russell | 435/226 |
| 454,575 | 6/1891 | Webber | 435/226 |
| 3,026,251 | 3/1962 | Wolf, Jr. et al. | 424/94.66 |

OTHER PUBLICATIONS

Sigma catalogue, p. 604, Feb. 1983.

*Primary Examiner*—David M. Naff
*Assistant Examiner*—Michael V. Meller
*Attorney, Agent, or Firm*—Rogers, Howell & Haferkamp

[57] ABSTRACT

A method for producing a composition having an inhibiting effect on production of tumor necrosis factor (TNF), and a method for inhibiting the production of TNF in vivo by administering the composition is provided. The composition comprises a solution of pepsin which has been rendered substantially proteolytically inactive by a series of sequential dialysis against running water, deionized water, and distilled water, respectively, for periods of time sufficient to substantially eliminate the proteolytic activity of the pepsin solution. The resulting composition is combined with a pharmaceutically acceptable carrier and administered in vivo to partially inhibit the production of TNF induced by a bacterial endotoxin.

5 Claims, No Drawings

PREPARATION OF PEPSIN SUBSTANTIALLY DEVOID OF PROTEOLYTIC ACTIVITY USING DIALYSIS

BACKGROUND OF THE INVENTION

The present invention relates to a procedure for producing a composition having an inhibiting effect on hyperproduction of the tumor necrosis factor (TNF) and which therefore is useful in the manufacture of pharmaceutical preparations. The advancement of scientific knowledge has made it possible to establish the participation of TNF in many pathological processes. TNF is normally produced by monocytes and/or macrophages. This cytokine, which was originally characterized by its tumor necrotic effect and which was subsequently identified as being homologous with cachectin, today is included in the group of substances known as inflammatory cytokines, i.e., those which are produced at inflammation sites by infiltrating mononuclear cells (Jan Vilcek and Tae H. Lee, in *J. Biol. Chem.*, Vol. 266 (1991), at pages 7313 to 7316). Its participation in modulating the manifestation of polymorphonuclear leukocyte adhesion antigens in this context has been described. The hyperproduction of TNF-$\alpha$ has been described in a large number of pathologies, such as cachexia, septic shock, rheumatoid arthritis due to other autoimmune disorders, parasitic infections, viral infections, etc. Therefore it is important that products be available which are pharmacologically equipped with the ability to inhibit the hyperproduction of TNF. In this context, the inhibition of the production of TNF has been described in various experimental models. For instance, E. Sampaio et al. (in *J. Exp. Med.*, Vol. 173 (1991), at pages 699 to 703) describe the inhibition by means of thalidomide, of the production of TNF by human monocytes stimulated in vitro by lipopolysaccharide (LPS); M. Gardina et al. (in *J. Exp. Med.*, Vol. 173 (1991), at pages 1305 to 1310) describe the effect of chlorpromazine, which consists of the reduction of serum levels of TNF in animals stimulated by LPS; S. Bily et al. (in *Int. J. Immunopharm.*, Vol. 12 (1991), at pages 31 to 36) have described the inhibiting effect of quinolones on the production of TNF by human monocytes. Similar effects have been described for indomethacin. The literature contains descriptions of the pharmacological properties of pepsin administered intravenously and with regard to its characteristic effect, i.e., the proteolytic effect. These include the effect on the formation of dental plaque (H. G. Scheider, E. Goebbels, and K. Puechner, in *Stomatol. DDR*, Vol. 36 (1986), at pages 433 to 438), on Masussi's nephritis (H. Ohnishi, in *Nippon Yakurigaku Zasshi*, Vol. 83 (1984), at pages 105 to 114), on autoimmune disorders in murine models (H. Ohnishi, in *Life Sci.*, Vol. 33 (1983), at pages 1641 to 1648), and on glomerulonephritis as produced by immunocomplexes (H. Ohnishi, in *Life Sci.*, Vol. 33 (1983), at pages 671 to 677).

SUMMARY OF THE INVENTION

The present invention describes a procedure for producing, from pepsin, a product derived from pepsin which has no proteolytic effect and which, when administered in the proper manner orally to mice, is capable of partially inhibiting the serum levels of TNF induced by a bacterial endotoxin (LPS).

DESCRIPTION OF PREFERRED EMBODIMENTS

The procedure for the production of a composition having an inhibiting effect on hyperproduction of the tumor necrosis factor (TNF), which is the object of the present invention, consists of a process of exhaustive and successive dialyses of an aqueous solution of a pepsin preparation, the aqueous solution having a defined concentration, and with the procedure occurring in three stages for which the time, the type and volumes of dialysis liquid, and the temperature are defined, followed by a process of drying by means of lyophilization.

During the process performed under the controlled conditions as described herein, the initial protein is modified by means of autolysis and denaturation with the loss of the characteristic initial proteolytic effect, and the new clinically applicable pharmacological property is obtained. The stages of the procedure are described below.

In the first stage, a solution of a pepsin preparation is prepared in deionized water, with the solution having a final concentration of 50 to 200 mg per $ml^{-1}$, with the solution being filtered if necessary.

In the second stage, after the solution obtained in the preceding stage has been introduced into a Visking type dialysis container having a molecular length of 6 to 14 kd, a first dialysis is performed with running water over a period of time of 2 to 6 days and at room temperature.

In the third stage, a second dialysis is performed, with a volume of deionized water which is from 50 to 1000 times the volume of the liquid to be dialyzed, over a period of time of 4 to 20 hours and at a temperature of 4° to 10° C.

In the fourth stage, a third dialysis is performed, with a volume of distilled water which is from 50 to 1000 times the volume of the liquid to be dialyzed, over a period of time of 8 to 30 hours and at a temperature to 4° to 10° C.

In the fifth stage, the dialysis liquid is frozen and dried by means of lyophilization.

In the sixth stage, the dried product obtained in the previous stage i used to prepare galenic forms of the product which are appropriate for oral or intravenous administration, with the forms being the ones which will be used in various biological tests. For oral administration, solid mixtures containing 1 to 5 percent $CaH(PO_4).2H_2O$ are prepared. For intravenous (IV) administration, extemporaneous solutions are prepared which have a concentration of 2 to 5 $\mu g$ per $ml^{-1}$ in an isotonic saline solution.

EXAMPLE

In a first stage, a quantity of 0.1 to 2.5 grams of commercial pepsin at a grade of 1:3000 is weighed and dissolved in a volume of 10 to 200 ml of deionized water. If the resulting solution is not clear, it is filtered through a 0.45 $\mu$ cellulose filter.

In a second stage, the aqueous pepsin solution is introduced into a Visking type dialysis container having a molecular length in the range from 10 to 14 kd and which was first washed in water at a temperature of 60° C. and then exhaustively rinsed with distilled water. A flask is filed with running water and introduced into the dialysis container, and the mouth of the flask is placed under a stream of running water having a slow flow rate (e.g., 20 to 40 ml per $minute^{-1}$), thus ensuring the continuous renewal of the dialysis fluid. This step is performed at room temperature for a period of 2 to 6 days.

In a third stage, the dialysis container containing the dialyzed pepsin solution form the preceding stage is further dialyzed with a quantity of 1 to 10 liters of distilled water over a period of 4 to 20 hours and at temperature of 4° to 10° C.

In the fourth stage, the dialysis container containing the dialyzed pepsin solution form the preceding stage is dialyzed again, this time with a quantity of 1 to 10 liters of distilled water over a period of 8 to 30 hours and at a temperature of 4° to 10° C.

In the fifth stage, the dialyzed pepsin solution obtained in the preceding stage is frozen and lyophilized, and an hygroscopic white powder is obtained.

In the sixth stage, the galenic forms of the product for pharmacological tests are prepared. For oral administration, a quantity of 200 mg of the lyophilized product is weighed and mixed with a quantity of 10 grams of $CaH(PO_4).2H_2O$. Mixing is achieved by means of mechanical stirring. For IV administration, a solution is prepared which has a concentration of 2 to 5 µg per $ml^{-1}$ in an isotonic saline fluid.

The product obtained after the fifth stage, and more particularly the product described in the preceding example, has new biochemical and pharmacological characteristics which are different from those of the initial product. Such characteristics are shown in Table 1 and below.

The product obtained after the sixth stage of the procedure has been carried out, and which is the subject of the present invention, has the flowing biological effects:

1) The product, in the form of a 2 percent mixture with phosphate salt and administered at a dosage of 150 mg per $kg^{-1}$ to Balb/c mice over a period of 6 consecutive days, is capable of inhibiting 75 percent of the serum levels of TNF as induced by the IV injection of LPS administered 2.5 hours after administration of the last dose of the product.

2) The product, in the form of a solid 2 percent mixture with phosphate salt and administered at a dosage of 150 mg per $kg^{-1}$ Balb/c mice over a period of 1 or 4 consecutive days, produces an increase in the plasma level of corticosterone, such increase being estimated at 2 to 3 times the basal level 5 hours after administration of the last dose.

3) The product, in isotonic saline solution, was administered to Swiss mice at a single dose IV of 0.05 mg per $kg^{-1}$ and did not produce any anomalies in body weight or in the histology of the liver, spleen, kidneys, or mesenteric lymph nodes, either at 7 days or at 14 days after administration.

TABLE I

| | | | Biochemical Properties | | |
|---|---|---|---|---|---|
| Product | $\epsilon^{1\%}$ 1 cm, 280 nm | Fluorescence intensity at 340 nm (in water) (exc. 270 nm) | Percentage of protein (by weight) (as determined in accordance with Lowry*) | Percentage of sugars (by weight) (as determined in accordance with Dubois**) | Proteolytic activity (in arbitrary units) (as determined in accordance with Rinderknecht***) |
| Initial | 1.3 | 100 | 19 | 68 | 100 |
| Final | 6.8 | 500 to 600 | 95 | 5 | 0 to 20 |

*O.H. Lowry, et al., in J. Biol. Chem., Vol. 193 (1951), at pages 265 to 275.
**A. Dubois, K.A. Gilles, et al., in Anal. Chem., Vol. 28 (1956), at pages 350 to 356.
***H. Rinderknecht, et al., in Clin. Chim. Acta, Vol. 21 (1968), pages 197 to 203.

We claim:

1. A method of preparing an aqueous solution of pepsin to render it substantially devoid of proteolytic activity and capable of inhibiting the production of tumor necrosis factor (TNF), the method comprising the steps of:

preparing an aqueous pepsin solution;

performing a first dialysis step on the pepsin solution against running water for about 2 to about 6 days at about 23° C. to obtain a first dialyzed pepsin solution;

performing a second dialysis step on the first dialyzed pepsin solution against a volume of deionized water from about 50 to about 1000 times the volume of the first dialyzed pepsin solution for about 4 to about 20 hours at about 4° C. to about 10° C. to obtain a twice dialyzed pepsin solution;

performing a third dialysis step on the twice dialyzed pepsin solution against a volume of distilled water from about 50 to 1000 times the volume of the twice dialyzed pepsin solution for about 8 to about 30 hours at about 4° C. to about 10° C. to obtain a thrice dialyzed pepsin solution;

drying the thrice dialyzed pepsin solution; and recovering said dialyzed pepsin solution.

2. The method of claim 1 wherein said aqueous pepsin solution is prepared at a concentration of about 10 mg/ml to about 125 mg/ml.

3. The method of claim 2 wherein said pepsin is purified pepsin.

4. The method of claim 3 wherein said running water in said first dialysis step has a flow rate of 20–40 ml/minute.

5. The method of claim 2 wherein the thrice dialyzed pepsin solution has a proteolytic activity of less than about 20% of said aqueous pepsin solution.

* * * * *